US009393172B2

(12) United States Patent
Byrd

(10) Patent No.: US 9,393,172 B2
(45) Date of Patent: Jul. 19, 2016

(54) SPINAL TRACTION MACHINE AND METHODS

(71) Applicant: Kevin Samuel Byrd, Belhaven, NC (US)

(72) Inventor: Kevin Samuel Byrd, Belhaven, NC (US)

(*) Notice: Subject to any disclaimer, the term of this patent is extended or adjusted under 35 U.S.C. 154(b) by 295 days.

(21) Appl. No.: 14/160,585

(22) Filed: Jan. 22, 2014

(65) Prior Publication Data
US 2015/0202111 A1 Jul. 23, 2015

(51) Int. Cl.
A61F 5/00 (2006.01)
A61H 1/02 (2006.01)

(52) U.S. Cl.
CPC ....... *A61H 1/0222* (2013.01); *A61F 2250/0008* (2013.01); *A61H 2201/1253* (2013.01); *A61H 2201/149* (2013.01); *A61H 2201/163* (2013.01); *A61H 2201/1607* (2013.01); *A61H 2201/1635* (2013.01)

(58) Field of Classification Search
CPC .............. A61F 2250/0008; A61H 1/0222; A61H 2201/1253; A61H 2201/149; A61H 2201/1607; A61H 2201/163; A61H 2201/1635; A61H 1/0292; A61H 1/0218; A61H 2201/1215; A61H 2201/164; A61H 2201/1664; A61H 2203/0456; A61H 2201/0161; A61H 2201/0173; A61H 2201/1621
USPC ..................................... 602/32–39
See application file for complete search history.

(56) References Cited

U.S. PATENT DOCUMENTS

| 1,171,713 A | 2/1916 | Gilkerson |
| 1,374,115 A | 4/1921 | Roemer |
| 1,642,158 A | 9/1927 | Kubista |
| 2,470,161 A | 5/1949 | Glasin |
| 2,475,003 A | 7/1949 | Black |
| 2,622,950 A | 12/1952 | Nimmo |
| 2,774,349 A | 12/1956 | Judovich |
| 3,734,088 A * | 5/1973 | Tucker, Jr. ........... A61H 1/0222 602/33 |
| 3,741,200 A | 6/1973 | Morin |
| 4,356,816 A | 11/1982 | Granberg |
| 4,466,427 A | 8/1984 | Granberg |
| 4,608,969 A | 9/1986 | Hamlin |

(Continued)

FOREIGN PATENT DOCUMENTS

GB 862277 A 3/1961

OTHER PUBLICATIONS

DJO Global: "Triton DTS Traction Unit", http://www.djoglobal.com/products/chattanooga/triton-dts-traction-unit, Sep. 16, 2013.

(Continued)

*Primary Examiner* — Michael Brown
(74) *Attorney, Agent, or Firm* — NK Patent Law, PLLC

(57) ABSTRACT

A spinal decompression machine includes a portable frame, a user support element, a laterally positioned handle extending from the frame, and a drive mechanism operatively coupled to the handle. A force bar operatively coupled to the drive mechanism extends longitudinally beyond a longitudinal end of the frame. A harness is attached to the first force bar. The drive mechanism causes the force bar to move longitudinally upon rotation of the handle. A method of providing traction includes positioning a person in a face up position upon the user support element, attaching a harness to a neck or pelvis of the person, the harness attached to a cervical traction bar or a pelvic traction bar, and moving the cervical fraction bar and pelvic fraction bar simultaneously in a common longitudinal direction by moving a handle.

20 Claims, 4 Drawing Sheets

(56) References Cited

U.S. PATENT DOCUMENTS

| | | | |
|---|---|---|---|
| 5,052,378 A * | 10/1991 | Chitwood | A61H 1/0222 606/242 |
| 5,158,568 A | 10/1992 | Riddle et al. | |
| 5,308,359 A | 5/1994 | Lossing | |
| 5,667,529 A | 9/1997 | Butner | |
| 5,672,157 A | 9/1997 | Gallagher et al. | |
| 5,895,367 A * | 4/1999 | Mautoni | A61F 5/3776 602/32 |
| 7,108,671 B2 | 9/2006 | Saunders et al. | |
| 2003/0093022 A1 * | 5/2003 | Sund | A61H 5/04 602/33 |

OTHER PUBLICATIONS

Hill Laboratories Company: "Hill Anatomotor Roller Massage Table with optional Lumbar Traction, Cervical Traction and Variable Speed", http://www.hilllabs.com/chiropractic/Hill-Anatomotor-Traction-Massage.php, Sep. 16, 2013.

* cited by examiner

SPINAL TRACTION MACHINE AND METHODS

TECHNICAL FIELD

The present disclosure relates to therapeutic traction devices and systems. More particularly, the present disclosure relates to cervical and pelvic traction machines and methods.

BACKGROUND

Spinal decompression, also known as "traction," is a broad term including many treatments involving elongation forces being applied longitudinally to the human torso. Both lumbar decompression along the lower back and cervical decompression along the upper back and neck can be provided by applying traction to the human form. Such treatments are typically applied in a professional's facility for relief of pain for those patients suffering from many spinal ailments that cause back pain due to spinal compression.

Only minimal and inconsistent forces can be applied directly by human force without mechanical assistance. Some corrective procedures can be applied by hand without using any mechanism. For example, some spinal subluxations are treated by hand by chiropractors. Spinal decompression, however, may not be best served by sudden or inconsistent discomforting forces, to which a person under treatment may instinctively resist with muscle contractions, both intended and as an unintended reflexes. Muscle relaxation should occur in concert with traction for full benefit and patient comfort both physically and psychologically.

Traction machines are available for assisting professionals in patient treatment. A typical such machine, however, is not portable in that it is too bulky or heavy for easy movement or placement within a home. Typical machines also include powered motors and complicated control systems. Such elements are heavy and expensive, and they insert a needless degrees of separation between the hand of a user and the application of force, blocking intuitive feel. A patient being winched by a powered system may not be comforted by the sound or whirring motors and may resist the treatment, intentionally or otherwise, by contracting muscles affected by the fraction.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In at least one embodiment, a spinal decompression machine includes a portable frame having a first longitudinal end and a second longitudinal end opposite the first longitudinal end, a user support element connected to the frame, and a first rotatable handle extending from the frame and positioned laterally relative to the user support element. A drive mechanism, which includes a pinion gear, is operatively coupled to the first rotatable handle. A first force bar extends longitudinally beyond the first longitudinal end of the frame. The first force bar is operatively coupled to the drive mechanism. A first harness is attached to the first force bar. The drive mechanism operatively couples the first rotatable handle to the first force bar causing the first force bar to move longitudinally upon rotation of the first rotatable handle.

In at least one example, the drive mechanism operatively couples the first rotatable handle to the first force bar causing the first force bar to move longitudinally in a first longitudinal direction upon rotation of the first rotatable handle in a first rotational direction, and the first force bar to move longitudinally in a second longitudinal direction opposite the first longitudinal direction upon rotation of the first rotatable handle in a second rotational direction opposite the first rotational direction. In at least one example, the first rotatable handle is rotatable about a lateral axis perpendicular to the first and second longitudinal directions.

In at least one example, a second force bar operatively coupled to the drive mechanism extends longitudinally beyond the second longitudinal end of the frame, and a second harness is attached to the second force bar. In that example, the drive mechanism operatively couples the first rotatable handle to the second force bar causing the second force bar to move longitudinally upon rotation of the first rotatable handle. The drive mechanism may include a rigid traveling member that interconnects the first force bar to the second force bar and that constrains the first force bar and the second force bar to move longitudinally in unison upon rotation of the first rotatable handle. In at least one example, the traveling member is a traveling rack having a toothed track that engages the pinion gear.

In at least one example, the traveling rack has a roller engagement face opposite the toothed track, and the drive mechanism includes a first roller that contacts the roller engagement face preventing the toothed track from disengaging with the pinion gear. In at least one example, the drive mechanism also includes a second roller that contacts the roller engagement face preventing the toothed track from disengaging with the pinion gear. In at least one example the rollers are located on longitudinally opposite sides of a point of engagement of the toothed track and the pinion gear.

In at least one example: the first rotatable handle is connected to a first-stage rotational drive shaft; a first gear is mounted on the first-stage rotational drive shaft; the pinion gear is mounted upon a second-stage rotational drive shaft; and a spur gear is mounted on the second stage rotational drive shaft. The spur gear has teeth that engage teeth of the first gear, and the spur gear has more teeth than that of the first gear and more teeth than that of the pinion gear.

In at least one example, the first force bar has a vertical portion that extends vertically higher than the user support element.

In at least one example, the portable frame includes a laterally extending head-end wall defining the first longitudinal end, a laterally extending foot-end wall defining the second longitudinal end, a first sidewall that extends longitudinally from first lateral ends of the laterally extending head-end wall and foot-end wall, and a second sidewall that extends longitudinally from second lateral ends of the head-end wall and foot-end wall. The first sidewall and second sidewall define left and right lateral sides of the frame. In at least one example, longitudinally extending internal walls define a channel in which the drive mechanism is positioned.

In at least one example, the first force bar moves longitudinally in the same direction as tangential movement of a top edge of the first rotatable handle when the first rotatable handle is rotated.

In at least one example, the first rotatable handle is mounted upon a rotational drive shaft, and a second rotatable handle is mounted upon the rotational drive shaft extending from the frame and positioned laterally opposite the first rotatable handle.

In at least one embodiment, a method of providing traction includes: providing a machine having a first longitudinal end, a second longitudinal end opposite the first longitudinal end, a movable cervical traction bar extending longitudinally outward from the first longitudinal end, a movable pelvic traction bar extending longitudinally outward from the second longitudinal end, and a user support element between the first longitudinal end and the second longitudinal end; positioning a person in a face up position upon the user support element; attaching a harness to a neck or pelvis of the person, the harness attached to the cervical traction bar or the pelvic traction bar; and moving the cervical traction bar and pelvic traction bar simultaneously in a common longitudinal direction by moving a handle operatively coupled to the cervical traction bar and pelvic traction bar.

In at least one example, the person positioned upon the user support element moves the handle. In at least one example, the person positioned upon the user support element rotates in unison a first handle on a first lateral side of the person and a second handle on a second lateral side of the person. In at least one example, the handle is rotated about an axis that is perpendicular to the longitudinal direction. In at least one example, rotating the handle moves a portion of the handle in a tangential direction that is the same as the common longitudinal direction.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated. The drawings are not necessarily drawn to scale.

DETAILED DESCRIPTIONS

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Figure 4:
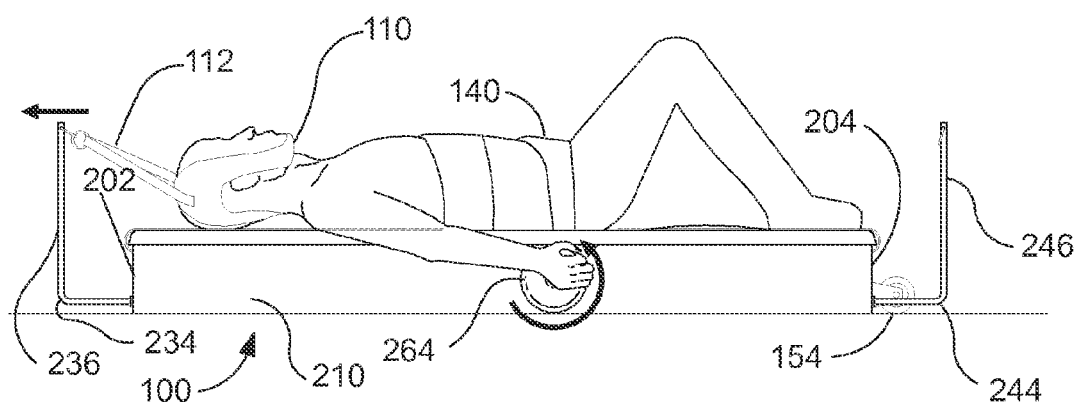
FIG. 4 is a side view of a user under cervical traction therapy by use of the machine of FIG. 1.
Figure 5:
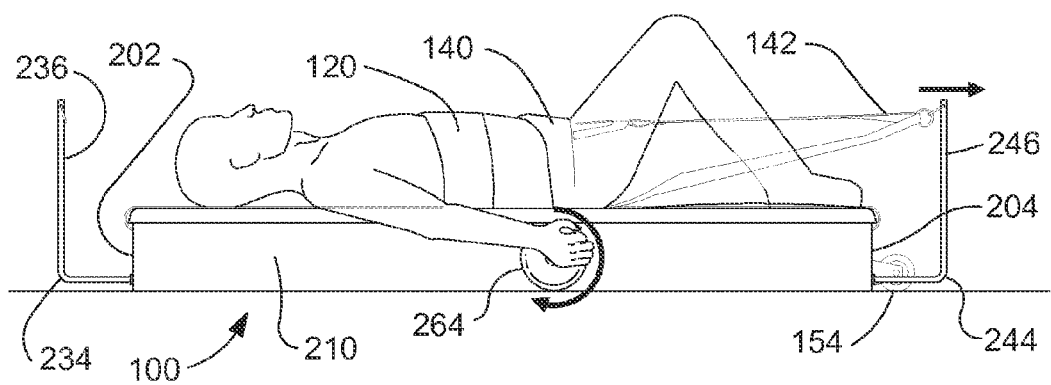
FIG. 5 is a side view of a user under pelvic traction therapy by use of the machine of FIG. 1.

The drawings illustrate a spinal decompression machine 100 that facilitates controlled tensioning of the human frame in at least two distinct areas: (1) upper back to neck; and (2) lumbar area to pelvic area. In use as shown in FIGS. 4 and 5, a user lies on the machine 100 and dons a cervical harness 110 for upper back to neck tensioning (FIG. 4). For lumbar area to pelvic area tensioning, the user dons a torso harness 120 and a pelvic harness 140 (FIG. 5). The user or an assistant such as a chiropractor or other health care provider then operates the machine 100 by use of rotational handles to actuate traveling head end and foot-end longitudinal force bars to which the cervical harness 110 and the pelvic harness 140 are respectively attached. Further descriptions of the use of the machine 100 commence below after the structural elements of the machine are described.

A box-like frame 200 is constructed of planar panel portions that define vertical walls. A head-end wall 202 and foot-end wall 204 define opposing longitudinal ends of the frame 200. A first sidewall 206 extends longitudinally from first lateral ends of the laterally extending head-end wall 202 and foot-end wall 204. A second sidewall 210 extends longitudinally from second lateral ends of the head-end wall 202 and foot-end wall 204. As such, the first sidewall 206 and second sidewall 210 define left and right lateral sides of the frame 200.

A medial pair of longitudinally extending internal walls 212 and 214 define a mechanism channel 216 in which a linear drive mechanism 220 is housed. The first internal wall 212 extends from the head-end wall 202 to the foot-end wall 204 between the mechanism channel 216 and the first sidewall 206. The second internal wall 214 extends from the head-end wall 202 to the foot-end wall 204 between the mechanism channel 216 and the second sidewall 206. The drive mechanism 220 includes a rigid traveling rack 222 captured within the mechanism channel 216. The longitudinally extending traveling rack 222 has an upward facing toothed track 224 and a downward facing smooth roller engagement face 226.

Figure 7:
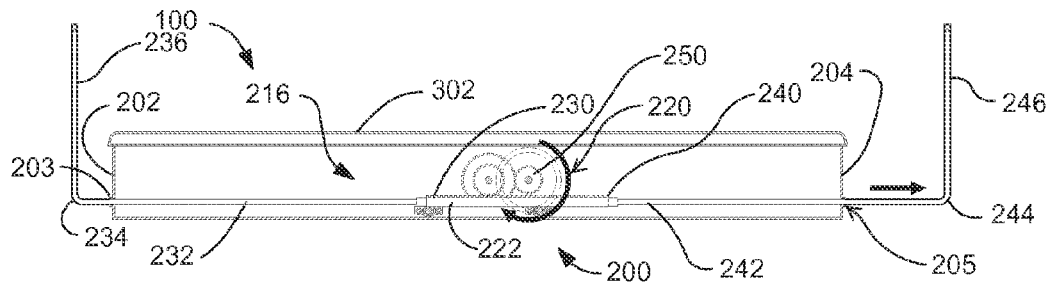
FIG. 7 is a cross-sectional side view taken as in FIG. 7, showing foot-end movement and force directed for pelvic traction.

A first longitudinal end 230 of the traveling rack 222 is connected to a horizontal portion 232 of a traveling head-end longitudinal force bar 234 (FIG. 7). A second longitudinal end 240 of the traveling rack 222 is connected to a horizontal portion 242 of a traveling foot-end longitudinal force bar 244. The traveling rack 222 is rigidly connected at its respective longitudinal ends to the head end and foot-end force bars 234 and 244. As such the force bars 234 and 244 are constrained to travel in unison longitudinally with the traveling rack 222 when the drive mechanism 220 receives sufficient torque via a laterally extending first-stage rotational drive shaft 250. When the drive mechanism 220 moves the traveling rack 222 in a longitudinal direction toward the head-end or tail-end of the frame, both the head-end force bar 234 and tail-end force bar 244 move simultaneously in that same direction.

Figure 6:
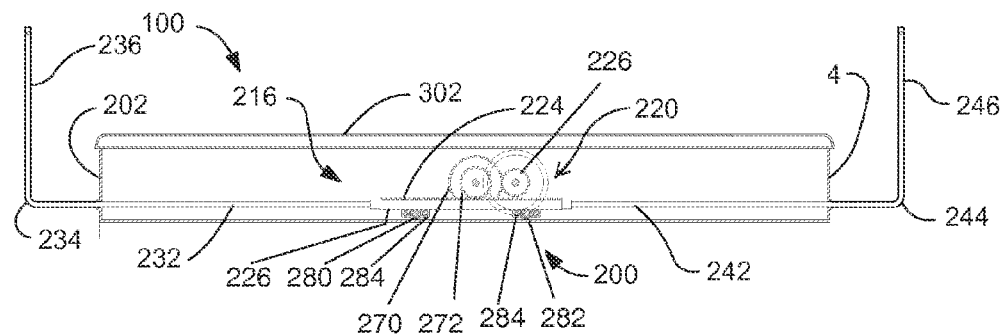
FIG. 6 is a cross-sectional side view of the machine of FIG. 1, taken along the line 6-6 in FIG. 3.

The head-end force bar 234 has a head-end vertical portion 236 (FIG. 6) extending upward at a right angle from the longitudinal end of the horizontal portion 232, which passes through a hole 203 (FIG. 7) formed through the head-end wall 202. The foot-end force bar 244 has a foot-end vertical portion 246 extending upward at a right angle from the longitudinal end of the horizontal portion 242, which passes through a hole 205 formed through the foot-end wall 204. The head-end force bar 234 bar, particularly the vertical portion 236 thereof, extends longitudinally beyond the frame 200 in the head-end direction. The foot-end force bar 244 bar, particularly the vertical portion 246 thereof, extends longitudinally beyond the frame 200 in the foot-end direction.

The holes 203 and 205 (FIG. 7) permit free longitudinal movement of the longitudinal force bars 234 and 244. For example, a dry-lubricant, a bushing, and other sliding engagements at the holes 203 and 205 are within the scope of these descriptions. As such, the vertical portions 236 and 246 of the force bars 234 and 244 travel longitudinally with the traveling rack 222 when the drive mechanism 220 receives sufficient torque via the laterally extending rotational drive shaft 250.

Figure 1:
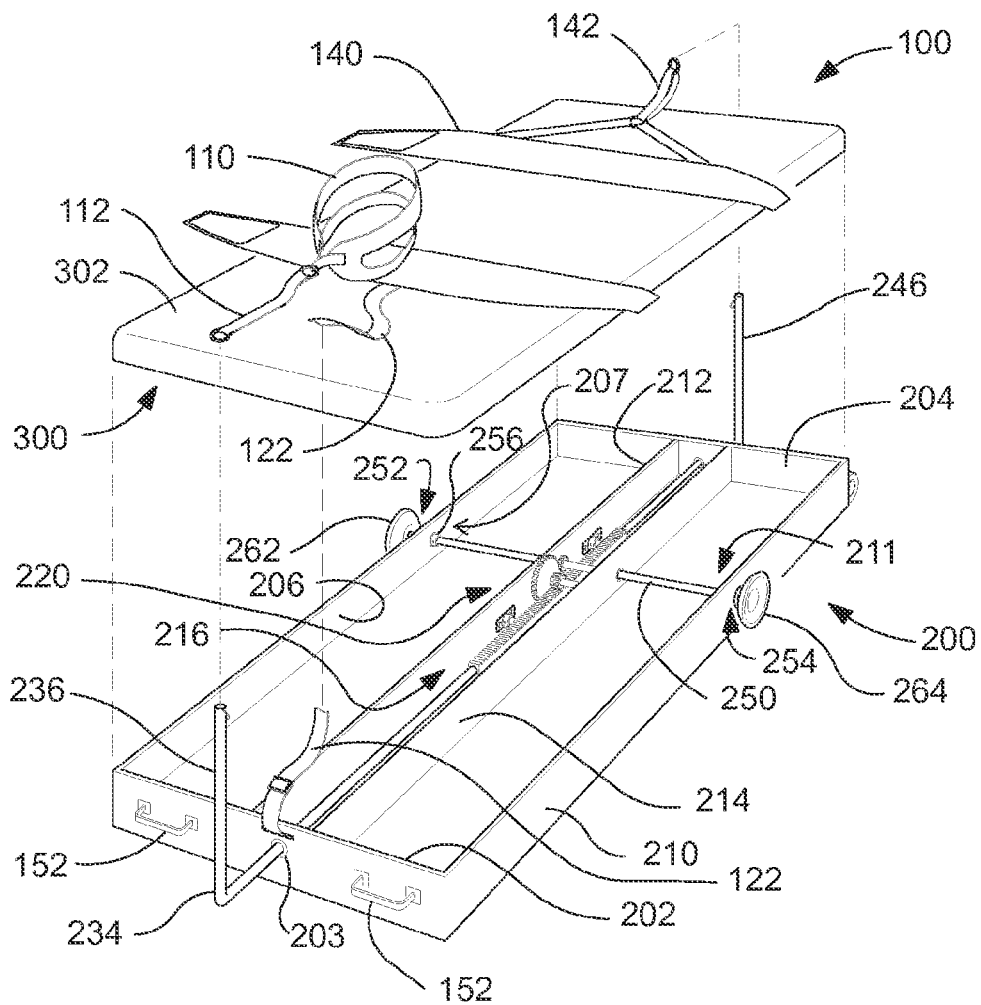
FIG. 1 is a partially exploded perspective view of a spinal decompression machine according to at least one embodiment.
Figure 2:
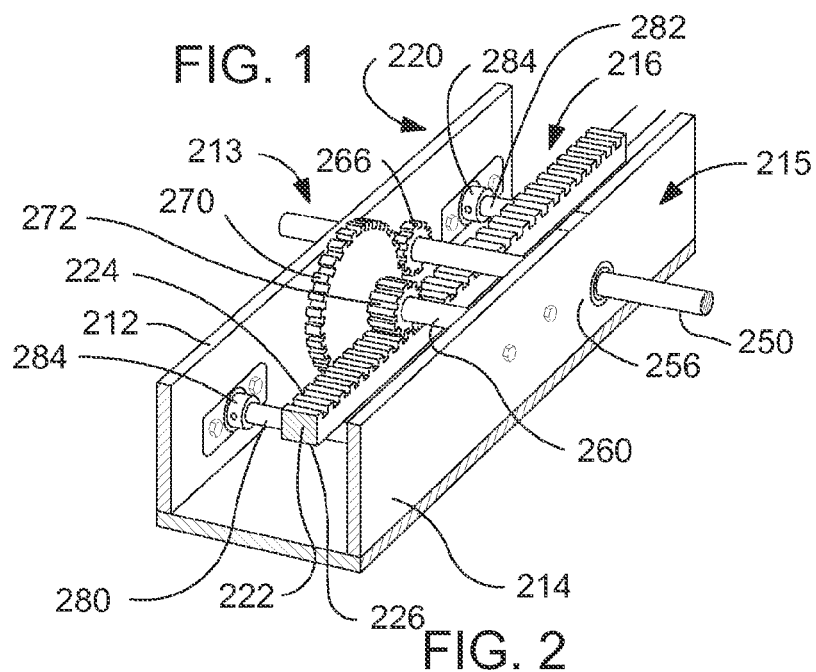
FIG. 2 is a perspective view of certain components of a drive mechanism for the machine of FIG. 1, according to at least one embodiment.

The rotational drive shaft 250 has opposing lateral ends 252 and 254 (FIG. 1) extending through holes 207 and 211 formed respectively through the first sidewall 206 and second sidewall 210. Medial portions of the rotational drive shaft 250 pass through holes 213 and 215 (FIG. 2) formed respectively through the internal walls 212 and 214. At each hole 207, 211, 213 and 215, a bearing coupling 256 is provided, for example as shown in FIGS. 1 and 2 at holes 207 and 215, to permit rotation of the rotational drive shaft 250 relative to the sidewalls 206 and 210 and internal walls 212 and 214.

The rotational drive shaft 250 is securely fixed in a longitudinal and vertical placement relative to the frame 200, with the drive shaft 250 extending laterally and able to rotate about a lateral axis passing through the holes 207, 211, 213, and 215. Similarly, the traveling rack 222 and force bars 234 and 244 are securely fixed in lateral and vertical placement relative to the frame 200, and are able to travel together longitudinally along a longitudinal axis passing through the holes 203 and 205 (FIG. 7) formed through the head-end wall 202 and foot-end wall 204 respectively.

Rotational handles 262 and 264 are respectively attached to the opposing lateral ends 252 and 254 of the first-stage rotational drive shaft 250 laterally outside of the box-like frame 200. The handles 262 and 264 are illustrated as disk-like handles having diameters that are greater than that of the first-stage drive shaft 250. Thus, mechanical leverage advantage is provided at the handles 262 and 264, which apply torque to the first-stage drive shaft 250 when grasped by a user who applies forces and/or torque to either or both of the handles 262 and 264. Due to the disk-like form of the rotationally movable handles 262 and 264 of the illustrated embodiment, movement of the handles 262 and 264 is perceived by the user as rotation of the handles. In other embodiments, for example where the movable handles are present as levers or other cranking structures, movement of the handles is perceived by the user as translation of the handles and/or a combination of translation and rotation.

The drive mechanism 220 includes the traveling rack 222 and a laterally extending second-stage rotational drive shaft 260, which has lateral ends that engage rotational mounts attached to the internal walls 212 and 214. As such, the second-stage drive shaft 260 is securely fixed in a longitudinal and vertical placement relative to the frame 200, with the second-stage drive shaft 260 extending laterally and able to rotate about a lateral axis passing through the rotational mounts. The rotational mounts include bearing or bushing couplings to permit rotation of the second-stage drive shaft 260 relative to the internal walls 212 and 214.

A first toothed pinion gear 266 (FIG. 2) is fixed to the first-stage rotational drive shaft 250 at a position within the mechanism channel 216. When the rotational drive shaft 250 is rotated, the pinion gear 266 rotates with the shaft 250 and drives the linear drive mechanism 220 in a mechanical coupling arrangement that ultimately converts torque and rotational movement at the handles 262 and 264 into linear force and linear movement.

A spur gear 270, having gear teeth that engage those of the first pinion gear 266, is fixed to the second-stage rotational drive shaft 260. The spur gear has a larger diameter and a greater number of teeth than those of the first pinion gear 260. A second pinion gear 272, having gear teeth that engage the toothed track 224 of the traveling rack 222, is also fixed to the second-stage drive shaft 260. The second pinion gear 272 has a smaller diameter and a lesser number of teeth than those of the spur gear 270. Thus, mechanical gear-ratio advantage is provided by the first pinion gear 266, spur gear 270, and second pinion gear 272.

Upon application of torque and/or rotation at the handles 262 and 264, longitudinal linear force and/or linear movement results at the traveling rack 222 and force bars 234 and 244. Due to present mechanical leverage and gear-ratio advantages as already described, a tangential force of any particular magnitude applied to an outer circular edge of either handle 262 and 264 results in a greater force being applied to the traveling rack 222 and force bars 234 and 244.

The drive mechanism 220 further includes roller bars 280 and 282 (FIGS. 2, 6) that extend laterally between the internal walls 212 and 214 and vertically support the traveling rack 222 to prevent flexure from causing disengagement of the toothed track 224 from the second pinion gear 272. The roller bars 280 and 282 contact the downward facing smooth roller engagement face 226 of the traveling rack 222. The roller bars 280 and 282 have lateral ends that engage rotational mounts 284 attached to the internal walls 212 and 214. As such, each roller bar 280 and 282 is securely fixed in a longitudinal and vertical placement relative to the frame 200, and is able to rotate about a respective lateral axis passing through the rotational mounts 284, which include bearing or bushing couplings to permit rotation of the roller bars 280 and 282. The traveling rack 222 is thus trapped from below by the roller bars 280 and 282 and from above by engagement of the toothed track 224 with the second pinion gear 272.

Advantageously, the roller bars 280 and 282 are located on longitudinally opposite sides of the point of engagement of the toothed track 224 and second pinion gear 272, and are spaced from the point of engagement so as not to immediately oppose the second pinion gear 272. In this arrangement, the rollers bars 280 and 282 prevent the traveling rack 222 from flexing out of engagement with the second pinion gear 272 without causing unwanted jamming.

Figure 8:
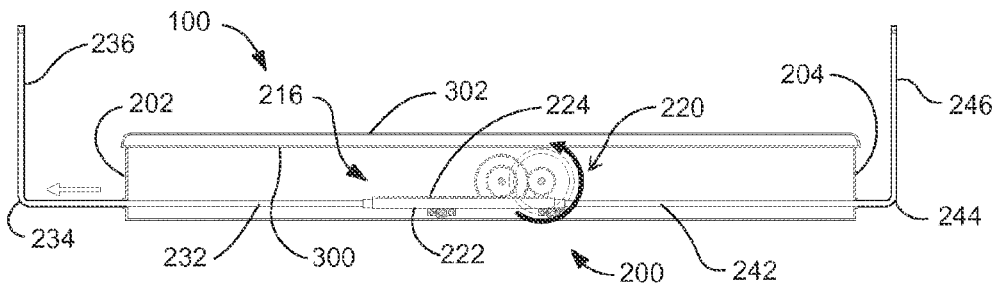
FIG. 8 is a cross-sectional side view taken as in FIG. 7, showing head-end movement and force directed for cervical traction.

A rigid planar user-support panel 300 covered by a soft user-comfort pad 302 (FIGS. 7-8) covers the top of the box-like frame 200. The panel 300 is attached to the upper margins of the vertical walls of the frame 200 and adds structural rigidity to the spinal decompression machine 100. The panel 300 and walls of the frame 200 in at least one embodiment are formed of sheet metal steel. The internal walls in at least one embodiment, for example, are formed as C-channel structures. Intersections of the walls, for example at the four corners of the frame 200, can be formed as weld-lines, supported by brackets, include rivets and other connectors, and can be formed as 90-degree bends such that some of the vertical walls are contiguous material portions of the same stock. Other constructions and materials are within the scope of these descriptions.

The pad 302 in at least one example includes a foam cushion placed over the user-support panel 300 and a flexible resilient covering wrapped over the foam cushion. In another embodiment, the pad 302 is a one-piece molded item of soft resilient material. Other constructions and materials are within the scope of these descriptions.

Figure 3:
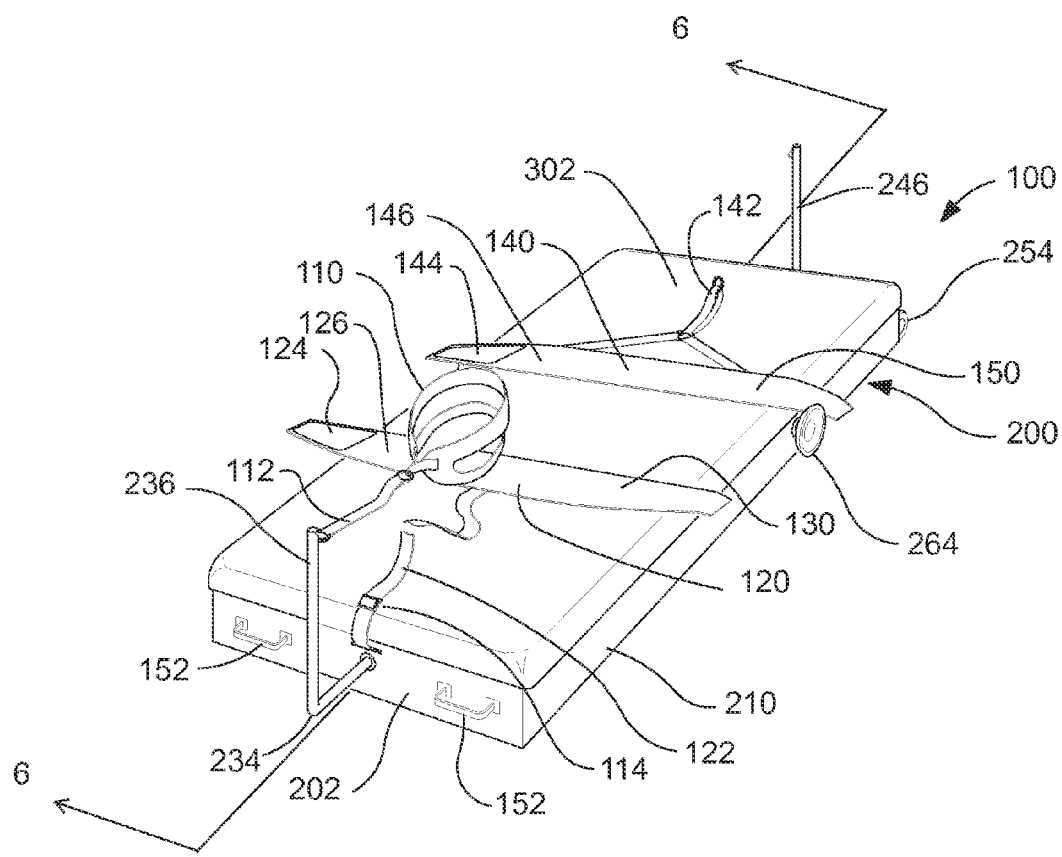
FIG. 3 is an assembled perspective view of the machine of FIG. 1.

The cervical harness 110 is attached by a tether 112 to the vertical portion 236 of the head-end force bar 234. The pelvic harness 140 is attached by a tether 142 to the vertical portion 246 of the foot-end force bar 244. The torso harness 120 is attached by a tether 122 to a head-end portion of the frame 200 to prevent its movement in the foot-end direction. In the illustrated example (FIG. 3), the tether 122 is attached to the head-end wall 202. Each tether may include an adjuster to permit a user to select a particular length according to preferred placement of the harnesses relative to the frame and force bars 234 and 244. For example, an adjuster 114 (FIG. 3) for adjusting the effective length of the torso harness tether 122 is shown in FIG. 3.

Each harness is constructed to encircle a body portion for tensional force application, and may include interconnecting fastening elements so as to securely retain its respective body portion. For example, the torso harness 120 has a hook-or-loop fastening first fabric patch 124 on a left-side torso harness flap 126, and a loop-or-hook fastening second fabric patch on a right-side torso harness flap 130. When the left-side torso harness flap 126 is brought into contact overlapping the right-side torso harness flap 130 with the torso harness 120 encircling the a human torso under the rib cage, the fastening first and second fabric patches maintain the flaps 126 and 130 in a secure but removable fashion. Similarly, the pelvic harness 140 has a hook-or-loop fastening first fabric patch 144 on a left-side torso harness flap 146, and a loop-or-hook fastening second fabric patch on a right-side torso harness flap 150.

The upper terminal ends of the vertical portions 236 and 246 (FIG. 6) of the head-end and foot-end force bars 234 and 244 extend vertically higher than the pad 302. This advantageously permits spinal decompression therapy forces to be applied above the pad 302 without clothing and such binding against the pad, without additional tissue compression or pinching, and without adding to the effective weight of the user upon the pad.

Handles 152 (FIGS. 1,3) are attached to the head-end wall 202 to facilitate a user grasping and transporting the spinal decompression machine 100. Wheels 154 (FIGS. 4-5) are attached to the foot-end wall 204 to further facilitate convenient transportation. For example, the head-end of the machine can be lifted by the handles 152 with the wheels 154 still contacting a floor or other support surface and the machine can be rolled about upon the wheels 154.

With regard to operation of the spinal decompression machine 100, as shown in FIG. 4, a user lying in a supine position (face up) upon the pad 302 dons at least the cervical harness 110 and turns the left-side rotational handle 262 (FIG. 1) and/or right-side rotational handle 264 (FIG. 4) in a first rotational direction causing head-end directional movement of the vertical portion 236 of the head-end force bar 234 until the cervical harness tether 112 carried by the force bar 234 is taut. The user then applies torque or force to the handle 262 and/or handle 264 to bring the desired tension to the upper back and neck portion of the user's body.

For lumbar decompression as shown in FIG. 5, a user lying upon the pad 302 dons at least the pelvic harness 140 around the hips and turns the left-side rotational handle 262 (FIG. 1) and/or right-side rotational handle 264 (FIG. 4) in a second rotational direction, opposite the first rotational direction, causing foot-end directional movement of the vertical portion 246 of the foot-end force bar 244 until the pelvic harness tether 142 carried by the force bar 244 is taut. The user then applies torque or force to the handle 262 and/or handle 264 to bring the desired tension to the lumbar area and pelvic area of the user's body. Advantageously, the rotational handles 262 and 264 are within reach of the user lying upon the pad 302. As such, a lying user may apply forces as desired while using the machine alone or under supervision.

The patient may also don the torso harness 120, encircling the human torso with the torso harness 120 under the rib cage, particularly when applying lumbar decompression. For cervical decompression, the patient lies in the same position on the machine but likely dons only the cervical harness 110. The weight of the patient on the pad is enough to hold them in place as the force required for cervical decompression is a fraction of that required for lumbar decompression.

By rotation of the handles 262 and 264 about a lateral axis, which is perpendicular to the longitudinal movement of the force bars 234 and 244, tangential movements of the circular edges of the handles 262 and 264 are longitudinal. Thus travel of the force bars 234 and 244 upon rotation of the handles 262 and 264 is intuitive from a user's perspective. Another intuitive advantage is provided in that the direction of force resulting at the traveling rack 222 and force bars 234 and 244 is the same as the direction of force applied to the top edges of the handles 262 and 264 due to the arrangement of the drive mechanism 220 as illustrated and described. Rolling the top edges of the handles 262 and 264 toward the foot-end of the frame 200 results in movement in the foot-end direction of the traveling rack 222 and force bars 234 and 244 for pelvic decompression and/or extension. Conversely, rolling the top edges of the handles 262 and 264 toward the head-end of the frame 200 results in movement in the head-end direction of the traveling rack 222 and force bars 234 and 244 for cervical decompression and/or extension.

In at least one embodiment, the spinal decompression machine 100 is approximately: 60 inches long; 20 inches wide; and 7 inches high. The machine 100 can be secured to the top of an existing table or positioned on a floor, depending on the modality of the patient. In at least one embodiment, the rotational handles 262 and 264 include 8-inch diameter aluminum hand wheels easily reached by the user for full control. In at least one embodiment, a 7:1 mechanical advantage is provided for gently stretching the spine with little effort from the patient.

Advantageously, the illustrated embodiment of the spinal decompression machine 100 is a non-electrical device having no power source. It is an entirely mechanical device that is mobile and can be used at home or in a professional's office or health care facility to treat common forms of back pain caused by spinal compression. The spinal decompression machine 100 may reduce lower back and neck pain by stretching or decompressing the spine. Conditions which may be treated include, but are not limited to: bulging or protruding discs, degenerative disc disease, sciatica, and other common causes of back pain. It may be used under prescription by a healthcare provider to provide spinal decompression. The spinal decompression machine 100 can apply therapeutic decompression force to relieve pressure on structures which may produce pain. Decompression can relieve pain by introducing a distraction force sufficient to reduce intradiscal pressure and impingement.

Advantageously, the spinal decompression machine 100 is a gear driven mechanical device that is operated by the patient or nearby assistant or caregiver. An advantage to having the patient solely operating the drive mechanism 220 is that it enables them to relax their muscles and enables a gentle and controlled stretching of the cervical or lumbar spine, as opposed to the patient being harnessed to a cable driven by an electric machine under automated or non-human control. A typical user will likely experience psychological ease in relaxing an affected body area due to complete control by the user of the force being applied. The gear driven mechanism 220 is believed to provide an intuitive and natural force feedback feeling to the user that is advantageous over other spinal tension systems that are driven by hydraulic mechanisms, cable and winch mechanisms, pneumatic actuators, jack screws, and chain drive systems. The rotational handles 262 and 264 move in unison to apply traction, thus the user can apply equal forces to the handles so as to promote symmetry and decompression without torso twisting or bending during treatment.

Advantageously, the spinal decompression machine 100 applies spinal traction therapy, particularly lumbar/pelvic decompression, without applying tension to the knee joints, ankle joints, and feet. Thus strain on the lower extremities is avoided. Gravity is not relied upon for the application of traction, thus users of all weights are able to selectively control any desired level of traction. The user-support panel 300 and user-comfort pad 302 are approximately planar support elements, and so spinal straightening is encouraged by the traction therapy of the machine 100 for spinal alignment without adjustable-level cushions or other elements that might adversely vertically or laterally manipulate the spine and cause spinal misalignment.

Advantageously, the upper terminal ends of the vertical portions 236 and 246 of the head-end and foot-end force bars 234 and 244 extend vertically higher than the pad 302. This advantageously permits spinal decompression therapy forces to be applies above the pad 302, which is particularly advantageous with regard to lumbar decompression, in which tension at an angle above zero is believed to be beneficial. Note that the pelvic harness tether 142 is taut at an angle above zero (horizontal) in FIG. 5.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A spinal decompression machine comprising:
   a portable frame having a first longitudinal end and a second longitudinal end opposite the first longitudinal end;
   a user support element connected to the frame;
   a first rotatable handle extending from the frame and positioned laterally relative to the user support element;
   a drive mechanism including a toothed gear, the drive mechanism operatively coupled to the first rotatable handle;
   a first force bar that extends longitudinally beyond the first longitudinal end of the frame, the first force bar operatively coupled to the drive mechanism; and
   a first harness attached to the first force bar,
   wherein the drive mechanism operatively couples the first rotatable handle to the first force bar causing the first force bar to move longitudinally upon rotation of the first rotatable handle.

2. A spinal decompression machine according to claim 1, wherein the drive mechanism operatively couples the first rotatable handle to the first force bar causing:
   the first force bar to move longitudinally in a first longitudinal direction upon rotation of the first rotatable handle in a first rotational direction; and
   the first force bar to move longitudinally in a second longitudinal direction opposite the first longitudinal direction upon rotation of the first rotatable handle in a second rotational direction opposite the first rotational direction.

3. A spinal decompression machine according to claim 2, wherein the first rotatable handle is rotatable about a lateral axis perpendicular to the first and second longitudinal directions.

4. A spinal decompression machine according to claim 1, further comprising:
   a second force bar that extends longitudinally beyond the second longitudinal end of the frame, the second force bar operatively coupled to the drive mechanism; and
   a second harness attached to the second force bar,
   wherein the drive mechanism operatively couples the first rotatable handle to the second force bar causing the second force bar to move longitudinally upon rotation of the first rotatable handle.

5. A spinal decompression machine according to claim 4, wherein the drive mechanism comprises a rigid traveling member that interconnects the first force bar to the second force bar and that constrains the first force bar and the second force bar to move longitudinally in unison upon rotation of the first rotatable handle.

6. A spinal decompression machine according to claim 5, wherein the toothed gear is a pinion gear and the traveling member is a traveling rack having a toothed track that engages the pinion gear.

7. A spinal decompression machine according to claim 6, wherein:
   the traveling rack has a roller engagement face opposite the toothed track; and
   the drive mechanism further comprises a first roller that contacts the roller engagement face preventing the toothed track from disengaging with the pinion gear.

8. A spinal decompression machine according to claim 7, wherein the drive mechanism further comprises a second roller that contacts the roller engagement face preventing the toothed track from disengaging with the pinion gear.

9. A spinal decompression machine according to claim 8, wherein the first roller and the second roller are located on longitudinally opposite sides of a point of engagement of the toothed track and the pinion gear.

10. A spinal decompression machine according to claim 6, wherein the drive mechanism further comprises:
    a first-stage rotational drive shaft to which the first rotatable handle is connected;
    a first gear mounted on the first-stage rotational drive shaft;
    a second-stage rotational drive shaft upon which the pinion gear is mounted;
    a spur gear mounted on the second stage rotational drive shaft, the spur gear having teeth that engage teeth of the first gear, the spur gear having more teeth than that of the first gear and more teeth than that of the pinion gear.

11. A spinal decompression machine according to claim 1, wherein the first force bar has a vertical portion that extends vertically higher than the user support element.

12. A spinal decompression machine according to claim 1, wherein the portable frame comprises:
    a laterally extending head-end wall defining the first longitudinal end;
    a laterally extending foot-end wall defining the second longitudinal end;
    a first sidewall that extends longitudinally from first lateral ends of the laterally extending head-end wall and foot-end wall;

a second sidewall that extends longitudinally from second lateral ends of the head-end wall and foot-end wall, the first sidewall and second sidewall defining left and right lateral sides of the frame.

13. A spinal decompression machine according to claim 12, further comprising a pair of longitudinally extending internal walls between which a channel is defined in which the drive mechanism is positioned.

14. A spinal decompression machine according to claim 1, wherein the first force bar moves longitudinally in the same direction as tangential movement of a top edge of the first rotatable handle when the first rotatable handle is rotated.

15. A spinal decompression machine according to claim 14, further comprising:
- a rotational drive shaft upon which the first rotatable handle is mounted; and
- a second rotatable handle extending from the frame, positioned laterally opposite the first rotatable handle, and mounted upon the rotational drive shaft.

16. A method of providing fraction comprising:
providing a machine having a first longitudinal end, a second longitudinal end opposite the first longitudinal end, a movable cervical traction bar extending longitudinally outward from the first longitudinal end, a movable pelvic traction bar extending longitudinally outward from the second longitudinal end, and a user support element between the first longitudinal end and the second longitudinal end;

positioning a person in a face up position upon the user support element;

attaching a harness to a neck or pelvis of the person, the harness attached to the cervical traction bar or the pelvic traction bar; and moving the cervical traction bar and pelvic traction bar simultaneously in a common longitudinal direction by moving a handle operatively coupled to the cervical traction bar and pelvic traction bar.

17. A method of providing traction according to claim 16, wherein moving the cervical traction bar and pelvic traction bar simultaneously in a common longitudinal direction by moving a handle comprises the person positioned upon the user support element moving the handle.

18. A method of providing traction according to claim 17, wherein moving the handle comprises the person positioned upon the user support element rotating in unison a first handle on a first lateral side of the person and a second handle on a second lateral side of the person.

19. A method of providing traction according to claim 16, wherein moving a handle comprises rotating the handle about an axis that is perpendicular to the longitudinal direction.

20. A method of providing traction according to claim 19, wherein rotating the handle comprises moving a portion of the handle in a tangential direction that is the same as the common longitudinal direction.

* * * * *